(12) United States Patent
Winger et al.

(10) Patent No.: US 6,251,600 B1
(45) Date of Patent: *Jun. 26, 2001

(54) HOMOGENEOUS NUCLEOTIDE AMPLIFICATION AND ASSAY

(76) Inventors: Edward E. Winger, 470A Cola Ballena, Alameda, CA (US) 94501; David E. Hargrove, 5799 Arlene Way, Livermore, CA (US) 94550

( * ) Notice: Subject to any disclaimer, the term of this patent is extended or adjusted under 35 U.S.C. 154(b) by 0 days.

This patent is subject to a terminal disclaimer.

(21) Appl. No.: 09/218,114

(22) Filed: Dec. 21, 1998

Related U.S. Application Data (63) Continuation-in-part of application No. 08/687,662, filed on Jul. 26, 1996, now Pat. No. 5,853,990.

(51) Int. Cl.[7] ............................ C12P 19/24; C07H 21/02; C07H 21/04; C07H 21/00

(52) U.S. Cl. ............................ 435/6; 435/91.1; 435/91.2; 536/23.1; 536/24.3; 536/25.32

(58) Field of Search ........................... 435/91.2, 6, 91.1; 536/24.3, 23.1, 25.32

(56) References Cited

U.S. PATENT DOCUMENTS

| | | | |
|---|---|---|---|
| 4,775,619 | 10/1988 | Urdea | 435/6 |
| 5,118,605 | 6/1992 | Urdea | 435/6 |
| 5,149,625 | 9/1992 | Church et al. | 435/6 |
| 5,268,289 | 12/1993 | Dahl et al. | 435/199 |
| 5,348,853 | 9/1994 | Wang et al. | 435/6 |
| 5,367,066 | 11/1994 | Urdea et al. | 536/24.3 |
| 5,391,480 | 2/1995 | Davis et al. | 435/6 |
| 5,430,136 | 7/1995 | Urdea et al. | 536/24.3 |
| 5,512,441 | 4/1996 | Ronai | 435/6 |
| 5,552,538 | 9/1996 | Urdea et al. | 536/24.3 |
| 5,556,773 | 9/1996 | Yourno | 435/91.2 |
| 5,567,583 | 10/1996 | Wang et al. | 435/6 |
| 5,573,906 | 11/1996 | Bannwarth et al. | 435/6 |
| 5,639,611 | 6/1997 | Wallace et al. | 435/6 |
| 5,643,765 | 7/1997 | Willey | 435/91.2 |
| 5,656,461 | 8/1997 | Demers | 435/91.1 |
| 5,660,988 * | 8/1997 | Duck et al. | 435/6 |
| 5,674,717 | 10/1997 | Backus et al. | 435/91.2 |
| 5,691,146 | 11/1997 | Mayrand | 435/6 |
| 5,700,642 | 12/1997 | Monforte et al. | 435/6 |
| 5,712,386 | 1/1998 | Wang et al. | 536/24.33 |
| 5,714,330 | 2/1998 | Brenner et al. | 435/6 |
| 5,716,784 | 2/1998 | Di Cesare | 435/6 |
| 5,723,294 | 3/1998 | Glass et al. | 435/6 |
| 5,723,591 | 3/1998 | Livak et al. | 536/22.1 |
| 5,741,678 | 4/1998 | Ronai | 435/91.2 |
| 5,744,308 * | 4/1998 | Guillou-Bonnici et al. | 435/6 |
| 5,747,255 | 5/1998 | Brenner | 435/6 |
| 5,786,183 | 7/1998 | Ryder et al. | 435/91.2 |
| 5,792,607 | 8/1998 | Backman et al. | 435/6 |
| 5,804,375 | 9/1998 | Gelfand et al. | 435/6 |
| 5,811,239 | 9/1998 | Frayne | 435/6 |
| 5,814,492 | 9/1998 | Carrino et al. | 435/91.2 |
| 5,824,517 | 10/1998 | Cleuziat et al. | 435/91.2 |
| 5,830,655 | 11/1998 | Monforte et al. | 435/6 |
| 5,846,726 | 12/1998 | Nadeau et al. | 435/6 |
| 5,849,497 | 12/1998 | Steinman | 435/6 |
| 5,853,990 * | 12/1998 | Winger et al. | 435/6 |
| 5,858,665 | 1/1999 | Hepp et al. | 435/6 |
| 5,861,250 | 1/1999 | Stanley et al. | 435/6 |
| 5,861,256 | 1/1999 | Glass et al. | 435/6 |
| 5,866,336 | 2/1999 | Nazarenko et al. | 435/6 |
| 5,869,252 | 2/1999 | Bouma et al. | 435/6 |
| 5,871,902 | 2/1999 | Weininger et al. | 435/5 |
| 5,876,978 | 3/1999 | Willey et al. | 435/91.2 |

FOREIGN PATENT DOCUMENTS

| | | | |
|---|---|---|---|
| 0 232 967 B1 | 4/1993 | (EP) | C12Q/1/68 |
| 0 320 308 B1 | 11/1993 | (EP) | C12Q/1/68 |
| 0 333 465 B1 | 1/1994 | (EP) | C12Q/1/68 |

OTHER PUBLICATIONS

Duck et al. Probe amplifier system based on chimeric cycling oligonucleotides, Biotechniques, vol. 9(2). pp. 142–147, 1990.*

Cebula, T.A. et al., "Simultaneous Identification of Strains of *Escherichia coli* Serotype 0157:H7 and Thier Shiga–Like Toxin Type by Mismatch Amplification Mutation Assay–Multiplex PCR," J. Clin. Microbiol., Jan. 1995; vol. 33, No. 1, pp. 248–250.

Chiang, P–W et al., "Use of a Fluorescent–PCR Reaction to Detect Genomic Sequence Copy Number and Transcriptional Abundance," Genome Res., Oct. 1996, 6(10):1013–26.

Chou, Q. et al., "Prevention of pre–PCR mis–priming and primer dimerization improves low–copy–number amplifications," Nucleic Acid Res., Apr. 1992, vol. 20, No. 7, pp. 1717–1723.

(List continued on next page.)

*Primary Examiner*—Kenneth R Horlick
*Assistant Examiner*—Joyce Tung
(74) *Attorney, Agent, or Firm*—Nathan P. Koenig; Crosby, Heafey, Roach & May (57) ABSTRACT

The invention comprises homogeneous nucleotide amplification strategies and assays. The methods involve amplification of a target nucleic acid sequence that includes the use of a probe that forms a duplex with a target nucleic acid sequence having an enzymatically cleavable region. The probe may anneal to other nucleic acid sequences but only forms an enzymatically cleavable region if the nucleic acid sequence is complementary to the probe. In other embodiments, the probe is configured to act as a primer for the amplification reaction if it anneals to a target nucleic acid sequence and is enzymatically cleaved. The target nucleic acid sequences amplified by the methods of this invention may be assayed by labeling the probe, by employing a second probe having features of the invention or by other suitable methods. Preferably, the probes comprise an RNA portion that forms an RNase H cleavable duplex with DNA.

16 Claims, 2 Drawing Sheets

OTHER PUBLICATIONS

Gibson, U.E.M. et al., "A Novel Method for Real Time Quantitative RT–PCR," Genome Res., Oct. 1996, 6(10):995–1001.

Heid, C.A. et al., "Real Time Quantitative PCR," Genome Res., Oct. 1996, 6(10):986–94.

Higuchi, R. et al., "Simultaneous Amplifications And Detection Of Specific DNA Sequences," Bio/technology (NY), Apr. 1992, 10:4, 413–17.

Ju, J. et al., "Energy transfer primers: A new fluorescence labeling paradigm for DNA sequencing and analysis," Nat. Med., Feb. 1996, vol. 2, No. 2, pp. 246–249.

Ju, J. et al. "Fluorecence energy transfer dye–labeled primers for DNA sequencing and analysis," Proc. Natl. Acad. Sci. USA, May 1995, vol. 92, pp. 4347–4351.

Livak, K.J. et al., "Oligonucleotides with Fluorescent Dyes at Opposite Ends Provide a Quenched Probe System Useful for Detecting PCR Product and Nucleic Acid Hybridization," PCR Methods Appl., Jun. 1995, 4(6):357–62.

Nazarenki, I.A. et al., "A closed tube format for amplification and detection of DNA based on energy transfer," Nucleic Acids Res., Jun. 1997, vol. 25, No. 12, pp. 2516–2521.

Orum, H. et al., "Single base pair mutation analysis by PNA directed PCR clamping," Nucleic Acid Res., Nov. 1993, vol. 21, No. 23, pp. 5332–5336.

Seyama, T. et al., "A novel blocker–PCR method for detection of rare mutant alleles in the presence of an excess amount of normal DNA," Nucleic Acids Res., May 1992, vol. 20, No. 10, pp. 2493–2496.

Shibata, H. et al., "RNA–primed PCR," Genome Res., Nov. 1995, 5(4):400–3.

Tyagi, S. et al., "Molecular Beacons: Probes that Fluoresce upon Hybridization," Nat. Biotechnol., Mar. 1996, vol. 14, pp. 303–308.

Tyagi, S. et al., "Multicolor molecular beacons for allele discrimination," Nat. Biotechnol., Jan. 1998, vol. 16, pp. 49–53.

* cited by examiner

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear    (ii) MOLECULE TYPE: DNA (xi) SEQUENCE DESCRIPTION: SEQ ID NO:1:

GACCTGAAGC ACTTGAAGGA GAA 23

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:2:

AAAGCGGAAG AATGTGTCAG C 21

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (ii) MOLECULE TYPE: RNA     (xi) SEQUENCE DESCRIPTION: SEQ ID NO:3:

GUCUCUGCGG AAGCCGAUUU CAUCAUCAC 29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (ii) MOLECULE TYPE: RNA     (xi) SEQUENCE DESCRIPTION: SEQ ID NO:4:

GUCUCUGCGG GAGUCGAUUU CAUCAUCAC 29

(2) INFORMATION FOR SEQ ID NO:5:

(i) SEQUENCE CHARACTERISTICS:
        (A) LENGTH: 120 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:5:

CTTTGAGGCT GACCTGAAGC ACTTGAAGGA GAAGGTGTCT GCGGGAGCCG 50

ATTTCATCAT CACGCAGCTT TTCTTTGAGG CTGACACATT CTTCCGCTTT 100

GTGAAGGCAT GCACCGACAT 120

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: chimeric DNA:RNA (ix) FEATURE:
            (A) NAME/KEY: Enabled primer; base pairs 1-19 DNA and
                base pairs 20-27 RNA (xi) SEQUENCE DESCRIPTION: SEQ ID NO:6:

AGGAGAAGGT CTCTGCGGGA GCCGGAU                                                         27

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

AGGAGAAGGT CTCTGCGGG                                                                  19

(2) INFORMATION FOR SEQ ID NO:8:

(i) SEQUENCE CHARACTERISTICS:
            (A) LENGTH: 23 base piars
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

TCCTCTGATT CTCTGGTGTC ACC                                                             23

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

GATCACTGTT CTCAGCCACA ATTACT                                                          26

(2) INFORMATION FOR SEQ ID NO:10:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:10:

CCCUGUACCC GCGACUAUCC CUCUGUCA                                                        28

HOMOGENEOUS NUCLEOTIDE AMPLIFICATION AND ASSAY

RELATED APPLICATION

This application is a continuation-in-part of U.S. patent application Ser. No. 08/687,662, filed Jul. 26, 1996 now U.S. Pat. No. 5,853,990.

BACKGROUND OF THE INVENTION

This invention is directed to methods for amplifying desired nucleotide sequences and assaying the nucleotides produced by such amplifications.

Recent advances in the general field of molecular biology have made it possible to detect specific genes of clinical and commercial importance. The use of nucleic acid hybridization assays as a research tool for the detection and identification of a unique deoxyribonucleic acid (DNA) sequence or a specific gene in a complete DNA, a mixture of DNA's, or a mixture of DNA fragments have made it possible to diagnose human disease at the genetic level.

The most common techniques for detecting a specific gene sequence are hybridization-based assays. A specific nucleotide sequence of probe is marked with a detectable label, typically a radioactive label (isotopic) or chemical modification (non-isotopic). The detectable label is combined with the nucleic acid sample of interest, either in situ as part of intact cells or as isolated DNA or RNA fragments. The hybridization conditions should be those which allow the probe to form a specific hybrid with its complementary DNA or RNA target while not becoming bound to non-complementary DNA or RNA molecules. The target sample sequence can be either free in solution or immobilized on a solid substrate. The probe's detectable label provides a means for determining whether hybridization has occurred and, thus, for detecting the DNA or RNA target.

The recent advances in automated nucleic acid oligonucleotide (ribo- and deoxyribo-) syntheses and the polymerase chain reaction (ICR) method of DNA amplification have increased the power and sensitivity of nucleic acid hybridization assays. PCR is an in vitro method for the enzymatic synthesis of specific DNA sequences, using two deoxyoligonucleotide primers that hybridize to opposite strands and flank the specific target region of DNA that is to be amplified. The use of automated thermal cyclers allows a repetitive series of reaction steps involving template denaturation, primer annealing and the extension of the annealed primers by DNA polymerase resulting in the exponential accumulation of the specific target region of DNA whose termini are defined by the 5' end of the primers.

PCR technique is an extremely powerful method for amplifying nucleic acid sequences, however the detection of the amplified material may require additional manipulation and subsequent handling of the PCR products to determine whether the target region of DNA is present. For example, removal of labeled probe that has not come into contact with the target sequence significantly complicates typical hybridization assays. A more useful probe technique would minimize the number of additional handling steps currently required for the detection of the amplified material. Ideally, such a technique would combine the amplification and detection steps into a homogeneous system, thereby eliminating the need for a post amplification phase separation of target-contracted and target-non-contacted probe prior to signal detection.

Prior art nucleotide detection strategies generally fall into two categories. The first is amplification of the target material to improve the efficacy of conventional detection methods. Livak et al., *PCR Methods and Applications*, 4:357 (1995), offers an example of this strategy by teaching the use of a reporter fluorescent dye and a quencher fluorescent dye attached to the 5' and 3' ends of an oligonucleotide probe. As the polymerase moves along the target DNA sequence in a 3' direction, its 5' nuclease activity first displaces and then cleaves the oligonucleotide probe, separating the reporter from the quencher. Thus, presence of target DNA sequence may be measured by detecting fluorescence of the reporter dye. Since this method depends on the 5' nuclease activity of the polymerase, significant constraints are placed on the design of probes that can be used. For example, the label must be attached to DNA and the probe must be designed to allow cleavage from the 5' end. Moreover, since one enzyme is being required to provide both polymerase and nuclease activity, it is not possible to independently select or optimize those events.

The second category features methods that rely on amplification of the probe signal produced by the target sequence, instead of amplifying the target directly. These methods require significant handling steps and are directed to an end point analysis as opposed to a kinetic, real time determination of target sequence presence. For example, U.S. Pat. Nos. 4,876,187 and 5,011,769, Duck et al., *Bio Techniques*, 9:142 (1990) and Bekkaoui et al., *Bio Techniques*, 2:240 (1996) disclose a cycling probe method that employs probes comprising RNA, preferably DNA:RNA:DNA chimeras. The reaction is carried out isothermally, using a temperature at which the chimeric probes will anneal to the target DNA. An enzyme such as RNase H is used to digest the RNA portion of the probe and generate shorter, labeled oligonucleotides that dissociate at the reaction temperature. The target DNA sequence is then available for hybridization with another probe and, after a number of cycles, sufficient label has been generated to collect and detect. In general, these methods rely on immobilizing a portion of the label to allow for phase separation and signal recovery and measurement. Since these systems require amplification of the probe signal, they are designed to be used as an alternative to conventional target amplification strategies and require isothermal conditions. Further, the methods rely on phase separation for detection of the label, and thus, are not directed to homogenous systems. Also, the choice of probe design is limited because the nuclease activity of polymerases could attack the DNA portion of a chimeric probe, generating false signal.

The difficulties posed in providing accurate detection of alleles or mutants that differ in sequence from related strains by as little as a single base exemplify the deficiencies of the prior art. Methods that use selective digestions with restriction enzymes followed by electrophoretic separation require substantial post-amplification handling. Homogeneous fluorogenic probes such as those described by Livak, supra, have only limited capacity to detect rare sequences despite being optimized for such discrimination. Similarly, probe amplification strategies such as taught in U.S. Pat. No. 5,660,988 to Duck et al. also are limited. These latter prior art methods suffer from drawbacks in at least two areas.

First, both target amplification and probe amplification strategies exploit the difference in annealing force of the probe between perfectly matched and non-perfectly matched sequences to generate different signal intensities with the respective sequences. The annealing force acting between a probe and its target sequence is the sum of the interactive forces acting between the individual base pairs. Signal intensity is thus related to the aggregate of all the interactions of the base pairs. Mismatch at a single base affects the interactive force in a graded manner. Strategies solely relying upon the difference in annealing force between target nucleic acid sequences are of limited usefulness for the detection and measurement of a nucleic acid sequence present in low concentration relative to the corresponding sequence present in high concentration.

Second, target amplification strategies entail the risk that rare sequences may be lost or drop-out during amplification where another sequence, present in significant excess over the rare sequence, is also being amplified. Consumption of substrate and production of inhibitory byproducts, base misincorporation in the dominant sequence, and generation of background signal from the dominant sequence all contribute to limiting detection of rare sequences.

Qualitative and quantitative detection of variable nucleic acid targets is also a limitation of prior art methods. Because signal generation by prior art detection strategies are affected by the annealing force between the probe and nucleic acid target, sequence mismatches will result in diminished signal generation. Quantitative assays may result in underestimation of the nucleic acid target while qualitative assays may provide false negative results. (Science Jun. 6, 1997, 276:1488–91).

To avoid these difficulties, probeless detection strategies have been devised. Higuchi and others have devised techniques based on the change in fluorescent signal generated by fluorogenic dyes upon binding to double-stranded DNA produced during the amplification reaction. (Biotechnology 10(4):412–417, April 1992) Nazarenko and others have incorporated a hair-pin structure labeled with energy transfer fluorophores at the 5' end of a primer used in PCR-based amplification. The primers are designed so that incorporation of the labeled primer into the amplification product relieves fluorescence quenching resulting in a detectable signal.

Strategies directed toward the inhibition of amplification of the target nucleic acid sequence have been devised. PNA (peptide nucleic acid) probes have been designed to compete with PCR primers under conditions where the annealing force of the fully complementary PNA probe is sufficient to prevent primer annealing and amplicon formation. Mismatched PNA probes, however, have insufficient annealing force to prevent primer annealing and amplicon formation. Kyger EM et al., "Detection of the hereditary hemochromatosis gene mutation by real-time fluorescence polymerase chain reaction and peptide nucleic acid clamping", Anal Biochem, 260:2, 142–8 (1998).

Probeless detection strategies have limited specificity and sensitivity because of the inability of these methods to distinguish amplification products generated by priming of non-complementary nucleic acid sequences or the generation of primer dimers. There remains a need for the development of strategies which satisfy the need for accurate qualitative and quantitative detection of the nucleic acid target while overcoming the difficulties caused by generation of non-specific amplification products.

Accordingly, there remains a need for improved amplification strategies. There is also a need for amplicaton strategies capable of providing homogenous detection of nucleic acid sequences, wherein the detection method is integrated into and compatible with amplification of the nucleotide. This is a further need for detection of amplification products that allow the use of more versatile probe designs. There is also a need for nucleotide amplification and detection methods that permit accurate discrimination of mutant and rare sequences. This invention satisfies these and other needs.

SUMMARY OF THE INVENTION

Generally, this invention comprises methods for amplifying a target nucleic acid sequence by providing a nucleotide amplification reaction mixture configured to amplify the target nucleic acid sequence, contacting the target nucleic acid sequence with a probe that is complementary to the target nucleic acid sequence and comprises at least one releasable probe portion, wherein the probe and the target nucleic acid sequence form a duplex having an enzymatically cleavable region wherein enzymatic cleavage of the probe results in the release of a releasable probe portion, and then contacting the probe and target nucleic acid sequence duplex with an enzyme capable of cleaving the enzymatically cleavable region to release the releasable probe portions.

One enhancement to the general method comprises attaching a label to at least one probe portion that is then detected when the enzyme cleaves and releases at least one probe portion. Further, to discriminate between a number of species of nucleic acid sequences, the amplification system can be configured so that the probe will anneal to additional nucleic acid sequences but not form an enzymatically cleavable region. Under the proper conditions, the probe annealed to the additional nucleic acid sequences prevents amplification of the additional nucleic acid sequences while amplification of the target nucleic acid sequence goes forward. In this way, the detection of rare sequences can be optimized. The target nucleic acid sequence may be assayed either by labeling any portion of the probe or by other suitable methods. The invention is adaptable to allow its use in conjunction with conventional PCR nucleotide assays.

In enabled primer embodiments, the probe is configured to act as a primer for the nucleotide amplification reaction. Preferably, the releasable probe portion is configured to block amplification activity so that when it anneals to the complementary target nucleic acid sequence, a duplex having an enzymatically cleavable region is formed. Subsequent cleavage releases the probe portion that blocks amplification. These embodiments are also useful for discriminating between closely related nucleotide sequences. As above, the enabled primer will anneal to additional nucleic acid sequences that are not perfectly complementary. However, since no enzymatically cleavable region is formed, the blocking portion of the probe is not released and amplification is suppressed. The enabled primer embodiments may be supplemented with the use of a second probe having features of the invention.

Preferred embodiments of the invention employ RNase H and probes composed, at least in part, of RNA that is cleavable by RNase H when it forms a duplex with DNA. The probe may also comprise non-cleavable portions that are composed of modified RNA bases or DNA bases. In other embodiments, it may be suitable to employ other template dependent enzymes having nuclease activity. In such instances, the probes should be tailored to the enzyme being used. Preferred embodiments of the invention are also directed to optimization of PCR amplification. However, the techniques may be adapted to other nucleotide amplification strategies.

DETAILED DESCRIPTION OF THE INVENTION

Definitions

The term "sample" or "specimen refers to nucleic acid isolated from an individual(s) or any nucleic acid containing entity, including but not limited to; skin, plasma, serum, spinal fluid, lymph fluid, synovial fluid, urine, tears, blood cells, organs, tumors, in vitro cell culture constituents, bacteria and viruses.

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose) and well as chimeric polynucleotides (containing 2-deoxy-D-ribose and D-ribose nucleotides), and to any other type of polynucleotide which is an N glycoside of a purine or pyrimidine base, or modified purine or pyrimidine bases. There is no conceived distinction in length between the term "nucleic acid", "polynucleotide" and "oligonucleotide", and these terms are used interchangeably. Thus, these terms include double-and single stranded DNA, as well as double- and single stranded RNA. The oligonucleotide is composed of a sequence of nucleotides, by preference at least 10–12 nucleotides, and more preferably at least 15–20 nucleotides coterminous to a region of the designated nucleotide sequence. "Coterminous" means identical to or complementary as defined below to the determined sequence.

The oligonucleotide is not necessarily limited to a physically derived species isolated from any existing or natural sequence but may be generated in any manner, including chemical synthesis, DNA replication, reverse transcription or a combination thereof. The terms "oligonucleotide" or "nucleic acid" refers to a polynucleotide of genomic DNA or RNA, cDNA, semisynthetic, or synthetic origin which, by virtue of its derivation or manipulation: (1) is not affiliated with all or a portion of the polynucleotide with which it is associated in nature; and/or (2) is connected to a polynucleotide other than that which it is connected in nature; and (3) is unnatural (not found in nature).

Oligonucleotides are composed of reacted mononucleotides to make oligonucleotides in a manner such that the 5' phosphate of one mononucleotide pentose ring is attached to the 3' oxygen of its neighbor in one direction via a phosphodiester linkage, and is referred to as the "5' end" end of an oligonucleotide if its 5' phosphate is not linked to the 3' oxygen of a mononucleotide pentose ring and subsequently referred to as the "3' end" if its 3' oxygen is not linked to a 5' phosphate of a subsequent mononucleotide pentose ring. A nucleic acid sequence, even if internalized to a larger oligonucleotide, also may be said to have 5' and 3' ends. Two distinct, non-overlapping oligonucleotides annealed to two different regions of the same linear complementary nucleic acid sequence, so the 3' end of one oligonucleotide points toward the 5' end of the other, will be termed the "upstream" or "forward" oligonucleotide and the latter the "downstream" or "reverse" oligonucleotide. In general, "downstream" refers to a position located in the 3' direction on a single stranded oligonucleotide, or in a double stranded oligonucleotide, refers to a position located in the 3' direction of the reference nucleotide strand.

The term "primer" may refer to more than one oligonucleotide, whether isolated naturally, as in a purified restriction digest, or produced synthetically. The primer must be capable of acting as a point of initiation of synthesis along a complementary strand (DNA or RNA) when placed under reaction conditions in which the primer extension product synthesized is complementary to the nucleic acid strand. These reaction conditions include the presence of the four different deoxyribonucleotide triphosphates and a polymerization-inducing agent such as DNA polymerase or reverse transcriptase. The reaction conditions incorporate the use of a compatible buffer (including components which are cofactors, or which affect pH, ionic strength, etc.), at an optimal temperature. In general, this is referred to as the "nucleotide amplification reaction mixture." The primer is preferably single-stranded for maximum efficiency in the amplification reaction. The term "enabled primer" is also used herein to refer to chimeric probes that are configured to be extendable by a polymerase once they are enzymatically cleaved, thus acting as a primer for the desired amplification reaction.

A complementary nucleic acid sequence refers to an oligonucleotide which, when aligned with the nucleic acid sequence such that the 5' end of one sequence is paired with the 3' end of the other. This association is termed as "antiparallel." Modified base analogues not commonly found in natural nucleic acids may be incorporated (enzymatically or synthetically) in the nucleic acids including but not limited to primers, probes or extension products of the present invention and may include, for example, inosine and 7-deazaguanine. Complementarity of two nucleic acid strands may not be perfect; some stable duplexes may contain mismatched base pairs or unmatched bases and one skilled in the art of nucleic acid technology can determine their stability hypothetically by considering a number of variables including, the length of the oligonucleotide, the concentration of cytosine and guanine bases in the oligonucleotide, ionic strength, pH and the number, frequency and location of the mismatched base pairs. The stability of a nucleic acid duplex is measured by the melting or dissociation temperature, or "Tm." The Tm of a particular nucleic acid duplex under specified reaction conditions is the temperature at which half of the base pairs have disassociated.

As used herein, the term "target sequence" or "target nucleic acid sequence" refers to a region of the oligonucleotide which is to be either amplified, detected or both. The target sequence resides between the two primer sequences used for amplification or as a reverse transcribed single-stranded cDNA product. The target sequence may be either naturally derived from a sample or specimen or synthetically produced. The term "additional nucleic acid sequence" is used to denote nucleic acid sequences that are similar to the target nucleic acid sequence but that differ by one or more base pairs. Examples of the relationship between the additional nucleic acid sequences and the target nucleic acid sequence are mutant/wild-type strains or alleles.

As used herein, a "probe" comprises a ribo-oligonucleotide which forms a duplex structure with a sequence in the target nucleic acid, due to complementarity of at least one sequence of the ribo-oligonucleotide to a sequence in the target region. The probe may be chimeric, that is, composed in part of DNA.

As discussed above, the probe may also be configured as an enabled primer. To prevent extension of the probe whether configured as a probe or an enabled primer, the 3' terminus is blocked. The addition of chemical moieties such as biotin, fluorescein, rhodamine and even a phosphate group on the 3' hydroxyl of the last deoxyribonucleotide base can serve as 3' end blocking groups and under specific defined cases may simultaneously serve as detectable labels or as quenchers. Furthermore, the probe may incorporate modified bases or modified linkages to permit greater control of hybridization, polymerization or hydrolyzation. As used herein, the terms "releaseable probe portion" and "non-releaseable probe portion" refer to probe fragments generated by enzymatic cleavage which have a Tm lower than and higher than the annealing temperature of the amplification reaction, respectively.

The term "label" refers to any atom or molecule that can be used to provide a detectable signal. Preferably, the signal is detectable in real time and is quantifiable. The detectable label can be attached to a nucleic acid probe or protein. Labels provide signals detectable by either fluorescence, phosphorescence, chemiluminescence, radioactivity, calorimetric (ELISA), X-ray diffraction or absorption, magnetism, enzymatic activity, or a combination of these. The terms "chemiluminescent and bioluminescent" include moieties which participate in light emitting reactions. Chemiluminescent moieties (catalyst) include peroxidase, bacterial luciferase, firefly luciferase, functionalized iron-porphyrin derivatives and others. The term "absorber/emitter moiety" refers to a compound that is capable of absorbing light energy of one wavelength while simultaneously emitting light energy of another wavelength or as heat energy. This includes phosphorescent and fluorescent moieties. The requirements for choosing absorber/emitter pairs are: (1) they should be easily functionalized and coupled to the probe; (2) the absorber/emitter pairs should in no way impede the hybridization of the functionalized probe to its complementary nucleic acid target sequence; (3) the final emission (fluorescence) should be maximally sufficient and last long enough to be detected and measured by one skilled in the art; and (4) the use of compatible quenchers should allow sufficient nullification of any further emissions.

As used in this application, "real time" refers to detection of the kinetic production of signal, comprising taking a plurality of readings in order to characterize the signal over a period of time. For example, a real time measurement can comprise the determination of the rate of increase of detectable product. Alternatively, a real time measurement may comprise the determination of time required before the target sequence has been amplified to a detectable level.

The terms "nuclease activity" and "enzymatic cleavage" refer to the activity of a template-specific nuclease, for example, RNase H. Other suitable enzymes include restriction enzymes and polymerases that have nuclease activity such as the 5' polymerase. As used herein, the term "RNase H" refers to an enzyme or an activity of an enzyme or of a process whether natural or unnatural whereby the RNA strand or region of a chimeric oligonucleotide or RNA containing region of a molecule capable of forming a hybrid duplex with DNA specifically degrades the RNA portion when in duplex with a DNA strand. The enzyme does not cleave single or double stranded DNA or RNA. A thernostable hybrid is available which remains active at the temperatures typically encountered during PCR. Generally, the enzyme will initiate nuclease activity whereby ribo nucleotides are removed or the ribo oligonucleotide is cleaved in the RNA:DNA duplex formed when the probe anneals to the target DNA sequence. It is conceivable that modified, or unnatural nucleotides may be cleaved by RNase H as used in this definition and thereby fall within the scope of this definition.

When used herein, the probe is said to be "matched", "perfectly matched" or "complementary" when the duplex of the probe and the target nucleic acid sequence comprises a region which is recognizable by an enzymatic cleaving activity of the amplification reaction mixture and releases a probe portion. When the enzyme cleaving activity of the amplification reaction mixture is RNase H, a probe region consisting of RNA must be matched with the complementary DNA of the nucleic acid target to assume a conformation which is recognizable by RNase H. The conformation is rendered unrecognizable by the enzymatic cleaving activity of the reaction mixture by the presence of one or more mismatched bases within or adjacent to the cleavable region of the probe. The number and placement of these base mismatches required to render the conformation unrecognizable by the enzymatic cleaving activity of the amplification reaction mixture may be varied by the conditions and sequences of the amplification reaction mixture.

When used herein, the term "RNA" or "ribo-oligonucleic acid" may refer to RNase H cleavable sequences when in hybrid duplex with DNA or may refer to unnatural nucleotides as 2'-Omethyl RNA and nucleotides with unnatural linkages such that the hybrid duplex with DNA is not cleavable by RNase H. However, the probes of the invention must comprise one or more nucleotides that are enzymatically cleavable when in a duplex with the target nucleic acid sequence if the probe is complementary to that sequence.

When used herein the term "primer-dimer" refers to the accumulated short PCR product that is roughly the size of the DNA duplex created by two adjoining primers. These products, however, are not strictly composed of a linear dimer of the two primers. There may be a few template-directed nucleotides between the two primer sequences. While primers are generated by both primers, structures have been described using only a single primer. Heretofore, all PCR reactions generate some primer-dimer artifacts. ("Target Selection and Optimization of Amplification Reactions" by David H. Persing, p. 96 in "Diagnostic Molecular Microbiology: Principles and Applications", David H. Persing, Thomas F. Smith, Fred C. Tenover, Thomas J. White, American Society for Microbiology, Wash., D.C., 1993.).

As used herein, the term "thermostable nucleic acid polymerase" refers to an enzyme which is relatively stable to heat when compared, for example, to nucleotide polymerases from E. coli and which catalyzes the polymerization of nucleotides. Generally, the enzyme will initiate synthesis at the 3'-end of the primer annealed to the target sequence, and will proceed in the 5'-direction along the template.

The term "hybridization or reaction conditions" refers to assay buffer conditions that allow selective hybridization of the labeled probe to its complementary target nucleic acid sequence. These conditions are such that specific hybridization of the probe to the target nucleic acid sequence is optimized while simultaneously allowing amplification of the target nucleic acid. The reaction conditions are optimized for co-factors, ionic strength, pH and temperature.

As used herein the term "hot start" refers to PCR reaction conditions wherein primer annealing to the nucleic acid target and extension during the first cycle of amplification is prevented until conditions including temperature are reached which mninimize non-specific priming events.

Among strategies devised to provide hot start conditions are the provision of thermally activated DNA polymerases which are inactive prior to their exposure to elevated temperature conditions.

As used herein, the term "enzyme" refers to proteins or other substances or combinations of substances and other materials such as metal ions that have catalytic properties owing to their powers of specific action upon their substrates. This includes the nucleolytic activity of RNase H upon the RNA strand of a complementary duplex of RNA and DNA.

General Method

The practice of this invention will employ, unless otherwise indicated, standard techniques of molecular biology, microbiology and recombinant DNA techniques, which are within the skill of the art.

Generally, this invention is directed to methods of optimizing nucleotide amplification and nucleotide assays. The strategies involve using a probe that forms a duplex with the desired target nucleic acid sequence having at least one enzymatically cleavable region. The probe may be configured so that it has an enzymatically cleavable region only if the target nucleic acid sequence and the probe are perfectly matched.

Preferred embodiments of the invention exploit the nuclease activity of RNase H. RNase H is an enzyme known to degrade the RNA moiety of RNA-DNA hybrid molecules. RNA:DNA duplexes are a substrate for RNase H due to the particular secondary structure. Thus, RNase H is active along the length of the RNA:DNA duplex without positional restriction and thus is not limited to either terminus. RNase H will cleave monoribonucleotides or small ribo-oligonucleotide fragments from the duplex which are destabilized to the point that they dissociate from the larger, complementary polynucleotide (DNA). Thus, cleavage does not depend on the characteristics of the 5' end. This property allows great flexibility in the design of suitable probes.

In the probe and primer embodiments of the present invention, a probe is added simultaneously with the PCR primers and RNase H at the start of PCR. The reaction conditions utilized allow for the probe to hybridize to the target nucleic acid sequence permitting the activity of the RNase H to cleave the probe. Under the reaction conditions utilized, the releasable probe fragments dissociate from the target nucleic acid sequence prior to PCR primer extension through the region complementary to the releasable probe portion or portions. When the probe is configured as an enabled primer, the release of the blocking probe portion provides an oligonucleotide suitable for polymerase extension. The probe may be labeled. The signal generated from cleavage and release of the probe fragments and detection of the labeled fragments provides a means for assaying the target nucleic acid sequence during its amplification.

An additional enhancement of the amplification process occurs if the probe is constructed to anneal to additional nucleic acid sequences that are not perfectly matched. Although the probe will anneal to such sequences, no enzymatically cleavable region is formed. Under the proper conditions, the probe anneals to the additional nucleic acid sequences but prevents primer extension by the DNA polymerase, and therefore, amplification of the additional nucleic acid sequences. Accordingly, the additional nucleic acid sequences generate no signal from a labeled probe and no signal can be detected from labeled probed directed to other regions of the nucleic acid sequence or from double-stranded DNA-binding agents. In such embodiments, the detection of rare sequences is enhanced. Although useful with conventional polymerases, the blocking effect of the probe can be enhanced by using a polymerase that does not displace the probe regardless of cleavage or by employing conditions that minimize such displacement. For example, fast cycling amplification can minimize the time available for the polymerase to displace the non-cleaved probe. Alternatively, known polymerases such as the 5' polymerase can be modified to suppress or remove 3' exonuclease activity.

Alternatively, the probe is an enabled primer, configured to act as a PCR primer once it has been cleaved by RNase H. The enabled primer is added simultaneously with the RNase H and any other necessary primers at the start of PCR. The reaction conditions utilized allow for the enabled primer to hybridize to the target nucleic acid sequence. Once the duplex is formed, the nuclease activity of RNase H cleaves and releases the blocking portion of the primer. Removal of the blocking portion allows polymerase extension of the enabled primer to amplify the target sequence. In these embodiments, it may be desirable to employ a second probe that is not configured to be an enabled primer and is labeled to provide a detectable signal.

This present invention differs from previously described PCR amplification strategies wherein the post-PCR amplified target nucleic acid sequence(s) are detected, for example, by hybridization to a probe which forms a stable duplex with that of the target sequence under stringent hybridization and wash conditions. In contrast to those known detection methods used in post-PCR amplifications, the present invention permits the detection of the target nucleic acid sequences homogeneously during amplification of the target nucleic acid sequence.

Furthermore, prior art attempts to suppress amplification of non-target nucleic acid sequences, such as the PNA clamps described above, require a specific blocker for each competing sequence. Any nucleic acid sequence that is not blocked runs the risk of being amplified along with the target nucleic acid sequence. As such, these methods require a knowledge of the possible non-target sequences that may not be available. Even if such knowledge is available, these methods still require the use of a multitude of blockers. In contrast, the methods of this invention can allow amplification only when the probe anneals to a complementary sequence. This has the effect of blocking all competing non-target sequences without the need to tailor the probe to each non-target sequence and without the requirement of knowing what types of competing non-target sequence might be present.

Although RNase H is particularly suitable in the practice of this invention, other enzymes having template-dependent nuclease activity can be employed. Naturally, the probe would have to be configured in accordance with the different enzyme. The methods of this invention are also easily adaptable to other nucleic acid amplification systems. For example, amplifications such as self-sustained sequence replication (3 SR), ligase chain reaction (LCR), nucleic acid sequence based amplification (NASBA), SDA, TMA, ISO-CR and LAT are with the scope of this invention.

In labeled probe embodiments of the present invention, a label is attached to the probe so that the cleaved monoribonucleotides or small ribo-oligonucleotides which are generated by the nuclease activity of the RNase H can be detected. Several strategies may be employed to distinguish the uncleaved labeled ribo- or chimeric oligonucleotide probes from the cleaved labeled probe fragments. This feature of the present invention allows identification of those nucleic acid containing samples or specimens which contain sequences complementary to the ribo- or chimeric oligonucleotide probe. The probe may be labeled by incorporating moieties detectable by spectroscopic, photochemical, biochemical, immunocherical, enzymatic or chemical means. The method of linking or conjugating the label to the probe depends, of course, on the type of label(s) used and the position of the label on the probe, but in general comprises any suitable means of attachment known in the art. Further, the label may be considered attached to a particular nucleotide even though the attachment may comprise one or more intervening nucleotides.

A number of detectable labels which would be suitable for use in this invention, as well as methods for their incorporation into the probe, are known in the art and include, but are not limited to, enzymes (e.g., alkaline phosphatase and horseradish peroxidase) and enzyme substrates, radioactive atoms, fluorescent dyes, chromophores, chemiluminescent/ bioluminescent labels, electrochemiluminescent labels, labeled receptor-ligand binding, labeled antibody-antigen coupling, or any other labels that may interact with each other to enhance, alter, or diminish a detectable signal in real time. Should the PCR be practiced using a thermo-cycler instrument, the label must be able to survive the high temperature cycling required in this automated process.

Preferably, two interactive labels may be used on a single probe while maintaining an appropriate spacing of the labels on the probe to permit the separation of the labels during enzymatic cleavage. In some instances it may be desirable to use a single probe having two different label moieties.

In a preferred embodiment, the interactive labels comprise a reporter (such as a fluorescein) and quencher (such as rhodamnine) fluorescent dye pair. Each dye is attached to the probe, separated by at least a 3–6 base sequence to provide an adequate substrate for RNase H. In its single stranded state, the probe has sufficient flexibility that the rhodamine comes into proximity with the fluorescein with enough frequency to quench the reporter. However, when the probe anneals to the target nucleic acid sequence and is digested by RNase H, the fluorescein is separated from the rhodamine, increasing the detectable reporter fluorescence. The fluorescence may be measured in any suitable way, including the LS-50B System (Perkin-Elmer). The system may be varied as necessary to accommodate other means of enzymatic cleavage.

A number of modifications may be made to the probe to maximize quenching prior to hybridization and release. In general, the dyes may be attached either at the termini or internally. Alternatively, the dyes may be attached internally to optimize detection characteristics. Or, the probe can be designed so that it forms a secondary structure, such as a hairpin, that brings the reporter and quencher into proximity when unhybridized. The use of ribo-oligonucleotides may be used to great advantage in this embodiment. RNA forms inherently more stable secondary structures than DNA or chimeric oligonucleotides. Accordingly, probes can be designed which very efficiently quench reporter fluorescence prior to hybridization leading to assay systems with very low background noise. Additionally, this technique may not be possible using conventional homogeneous assay systems because the DNA:DNA hairpin could be a substrate for the nuclease, leading to false release of the label.

In a similar embodiment, detection of the cleaved labeled probe can be achieved using fluorescence polarization. This technique is able to distinguish between large and small molecules based on molecular tumbling. Large molecules (e.g., intact labeled probe) tumble in solution much more slowly than small molecules. Upon linkage of a fluorescent moiety to the molecule of interest, this fluorescent moiety can be measured (and differentiated) based on molecular tumbling, thus differentiating between intact and digested probe. Detection may be measured during PCR using LS-50B fluorimeter (Perkin Elmer) or other device configured to detect a fluorescence polarization signal.

In another embodiment, two labeled ribo- or chimeric oligonucleotide probes are used, each complementary to separate regions of a double-stranded target region, but not to each other. For example, the presence of two probes can potentially double the intensity of the signal generated from a single label and may further serve to reduce product strand reannealing, as often occurs dung PCR amplification.

In yet other embodiments, the use of radioactive atoms, such as $^{32}P$, may be suitable for labeling and detection. Enzymatic methods for introducing $^{32}P$ into nucleic acids are known in the art, and include, for example, 5' end labeling with polynucleotide kinase, or random insertion by nick translation and the Klenow fragment. Labels at the 3' terminus may employ polynucleotide terminal transferase to add the desired moiety, such as for example, cordycepin $^{35}S$-dATP, and biotinylated dUTP. The labels may be attached to the ribo- or chimeric oligonucleotide probe directly or indirectly by a variety of techniques. Depending on the precise type of label used, the label might be located at the 5' or 3' end of the probe, located internally in the probe's nucleotide sequence, or attached to carbon spacer arms of various sizes and compositions to facilitate signal interactions. Using commercially available phosphoramidite reagents, one can produce oligomers containing functional groups (e.g., thiols or primary amines) at either terminus via an appropriately protected phosphoramidite. Enzymes can be detected by their activity on a secondary substrate.

Methods for introducing oligonucleotide functionalzing reagents to introduce one or more sulfhydryl, amino or hydroxyl moieties into the oligonucleotide probe sequence, typically at the 5' terminus are described in U.S. Pat. No 4,914,210. A 5' phosphate group can be introduced as a radioisotope by using polynucleotide kinase and $\gamma$-$^{32}P$-ATP to provide a reporter group. Biotin can be added to the 5' end by reacting an aminothymidine residue, introduced during synthesis, with an N-hydroxysuccinimide ester of biotin.

Oligonucleotide (DNA and RNA) derivatives are also available labels. For example, etheno-dA and etheno-A are known fluorescent adenine nucleotides which can be incorporated into an ribo-or chimeric oligonucleotide probe. Similarly, etheno-dC is another analog that could be used in probe synthesis. The probes containing such nucleotide derivatives may be hydrolyzed to release much more strongly fluorescent mononucleotides during PCR.

This invention also permits greater sensitivity in the amplification and detection of a target nucleic acid sequence in the presence of additional nucleic acid sequences that may vary by as little as one base pair. By constructing the probe or enabled primer so that the cleavable region falls over the site of the possible mismatch(es), a duplex with a cleavable region will be formed only with a nucleic acid sequence that is perfectly complementary to the probe. Although the duplex with a cleavable region only forms with perfect complementarity, the probe can still anneal to noncomplementary nucleic acid sequences. This both inhibits amplification of nucleotides that do not match the target nucleic acid sequence and suppresses generation of false signal. With the noncomplementary nucleic acid sequences, the annealed probe is not cleaved so it inhibits amplification of noncomplementary nucleic acid sequence in one of two ways. The blocking portion of the enabled primer is not cleaved and released without perfect complementarity. Alternatively, the labeled probe remains annealed to the nucleic acid sequence since it is not cleaved into releaseable portions, and this interferes with primer extension. Further, when used with a labeled probe, false signal is suppressed because the lack of a cleavable region prevents release of labeled probe fragments. The amplified sequence may then be detected concurrently or at a single time point preferably at the end of amplification.

Specific detection of perfectly matched target nucleic acid sequences is improved in this invention. The potential for background signal generation is diminished where amplification of mismatched nucleic acid sequences is prevented. Amplification of rare sequences is improved where amplification of the predominant, mismatched sequence is prevented preserving reaction components for amplification of the rare sequences. Amplification errors permitting misincorporation of a complementary base and inappropriate signal generation are prevented.

Probes useful in the practice of this invention have some general characteristics. Specifically, the 5' end of the probe should be adjacent to or within one to a few bases from the 3' end of the forward primer. The melting temperature of the probe should be higher than the melting temperature of the forward primer. The melting temperatures of the probe fragments after enzymatic cleavage should be lower than the extension temperature of the amplification reaction. Accordingly, when there is no enzymatic probe cleavage, the forward primer will melt off the target nucleic acid sequence strand prior to the probe preventing primer extension and amplification. However, when there is enzymatic probe cleavage, the probe fragments melt off the target sequence permitting unimpeded primer extension and amplification of the target.

The oligonucleotide primers and labeled probes may be prepared by a number of methods. Methods for preparing oligonucleotides (deoxy-, ribo-, and chimeric) of a specific sequence are known in the art, and include, for example, cloning and restriction of appropriate sequences, direct automated chemical syntheses and enzymatically. Such techniques include, for example, the phosphotriester method, that phosphodiester method, the diethylphosphoramidate method, and the solid support method.

The composition of the probes can be designed to inhibit nuclease activity. The incorporation of modified phosphodiester linkages (e.g., methyl phosphorylthioate or methylphosphonates) in the labeled probe during chemical synthesis may be used to prevent cleavage at a selected site. Depending on the length of the probe, the composition of its 5' complementary region, and the position of the label, one can design a probe to preferentially favor the generation of short or long labeled probe fragments for use in the practice of the invention. Great flexibility in the modification of the probes of this invention is possible so long as a probe/target sequence duplex offers an enzymatically cleavable region. For example, RNase H may cleave where 3 or more contiguous base pairs of an RNA:DNA sequence are RNA. Egli, M., N. Usman, S. Zhang, and A. Rich (1993) Crystal structure of an Okazaki fragment at 2-Å resolution. Proc. Natl. Acad. Sci. 89: 534–538.

To distinguish rare sequences that may vary from dominant strains by as little as one base pair, the portion of the probe designed to correspond to the enzymatically cleavable region should span the mismatch to provoke the greatest disruption and prevent formation of the region. The mismatch can be designed to occur at the central base pair of the enzymatically cleavable region. It is conceivable that the site of mismatch may also result in disruption of the enzymatically cleavable site where the mismatch is located at other bases within the enzymatically cleavable region or at bases in the adjacent region of the enzymatically non-cleavable region.

In the case of a probe comprised entirely of RNA bases, a single base may correspond to the enzymatically cleavable region since the entire RNA would be A-Form. RNase H may need only a single enzymatically cleavable base if the adjoining RNA or other A-Form pairing bases are a non-enzymatically cleavable, such as 2'O-methyl bases.

In the practice of this invention, it is often desirable to control the melting temperature of the primers and the probe. For example, in the probe and primer embodiments, the labeled probe must anneal to its complementary nucleic acid before primer extension polymerization reaches this duplex region. The invention allows for significant optimization of this characteristic as opposed to the prior art systems limited to DNA oligonucleotide probes. RNA:DNA hybrids are generally known to have a higher melting temperature than DNA:DNA or chimeric:DNA hybrids of the same base composition permitting greater specificity. The length of complementary nucleic acids is also known to effect the hybridization rate and the relative stability of the duplexes. Shorter nucleic acid molecules generally require a cooler temperature to form sufficiently stable hybrid complexes with the target nucleic acid. Therefore, the probe can be designed to be longer than the primer so that the labeled probe anneals preferentially to the target at higher temperatures relative to primer annealing. Furthermore, the addition of a denaturation solution such as formamide allows for an optimal temperature for the association of RNA:DNA hybrids as compared to DNA:DNA hybrids.

One can also vary the base composition of the primers and the probe to affect thermal stability. For example, the nucleotide composition of the probes can be chosen to have greater G/C content and, consequently, greater thermal stability than the primer(s). One skilled in the art can then utilize the thermocycling parameters to take advantage of the differential thermal stability of the labeled probe(s) and primer(s). Following the denaturation step in thermocycling, one could employ an intermediate temperature which is permissible for probe annealing and RNase H cleavage but not primer binding, and then the temperature can be further reduced to permit primer annealing and extension by the DNA polymerase.

In enabled primer embodiments, the first probe is configured as a primer but is altered so that the 3' end is blocked preventing polymerase extension of the primer. The nuclease activity of the template-dependant enzyme cleaves the clearable region when annealed to target nucleic acid sequence perfectly complementary in the cleavable region but does not cleave when there is a mismatch. The enabled primer is designed so that the 3' fragment generated by enzymatic cleavage can not remain hybridized to the target DNA strand during amplification while the 5' fragment does. Specifically, the Tm of the releasable 3' fragment is lower than the annealing temperature of the amplification reaction and the Tm of the non-releasable 5' fragment is higher. Polymerase extension of the 5' fragment of the primer is enabled because the primer is freed of the 3' blocking group. Preferably, the enabled primer is labeled with a reporter and quencher fluorochrome permitting the generation of detectable signal upon enzymatic cleavage. Alternatively, a detectable signal can be generated by a second probe or a DNA-binding agent or dye.

The enabled primer method permits the use of more stringent conditions than permitted by prior art. Primer design is not constrained as in probe based, real time methods, where the primers must have a significantly lower Tm than the probe. Further, prior art probeless detection methods are constrained to reaction conditions where hybridization conditions of the double-stranded binding agents or hybridization conditions of the 5' hairpin is optimum. These conditions may not permit optimization for the most stringent reaction conditions. Enabled primers may be designed to anneal and extend at higher temperatures diminishing problems related to secondary structure. Such conditions minimize problems encountered in multiplex assays.

Further, in the enabled primer embodiments, nucleotide amplification can occur at temperatures lower than conventional PCR. Specifically, PCR amplification with an enabled primer does not require conventional "hot start" conditions. PCR is hampered by the production of primer dimers and by the inappropriate priming and subsequent amplification of non-complementary nucleic acid sequences. A variety of techniques within the prior art minimize these effects. These techniques limit priming to stringent conditions in part by selection of an annealing temperature which is sufficiently high that non-specific hybridization is minimized. However, such priming is difficult to avoid prior to the first cycle of amplification because the ingredients of the amplification reaction are assembled at ambient or room temperatures where non-specific annealing is enhanced. Various strategies have been devised which prevent subsequent primer extension from the primers annealed to these mismatched targets. These include providing a thermally activated form of DNA polymerase. Such methods are generally known as "hot start" methods. The enabled primer as provided is not capable of extension until it anneals to a perfectly matched nucleic acid target. The enabled primer can not be extended unless it is annealed to its specific target. Therefore, hot-start conditions are unnecessary to prevent non-specific amplification.

One useful application for the methods of this invention includes genetic screening for detection of variations in the number of repeated short sequences such as trinucleotide repeats also known as tandemly repeated sequences. Most of these repeat sequences are non-coding, but some such as CAG repeats are found in neurologic diseases such as Huntington's Disease and code for glutamine. The resulting expanded polyglutamine regions have pathologic consequences. DNA-binding methods can be used to make a rough determination of sequence length. Different length alleles have different Tm's which can be demonstrated by a loss in fluorescence as the Tm is reached causing complementary strand dissociation and loss of dye binding. However, these techniques may not be sensitive enough to detect small differences in the number of repeat sequences or accurately quantify them.

The use of dye-binding signal generation in conjunction with the enabled primer embodiments may permit ratioing of the signals and comparing the signals or their ratios to standards which are varied in the number of tandemly repeated sequences. The technique may be used with or without melting point "scanning". Alternatively, especially in embodiments without labeling, the amplification products can be sized by gel electrophoresis. The optimized amplifications using the probes of this invention should produce the most specific product.

Amplification and assay with the enabled primer embodiments of this invention offer a number of advantages over the prior art. As discussed above, conventional probe-based methods may miss or underestimate the amount of amplified product generated. The methods of the invention also block primer-dimer generation.

Further, since the probe functions as a primer, short amplicons using short primers can be selected within the constraints of prior art primers which tend to generate non-specific amplification products when the lower temperatures required for the annealing of short primers are used. Prior art methods used to distinguish non-specific amplification products from amplification of target nucleic acid sequences requires the selection of longer amplicons which permit their discrimination by differences in their melting points or by electrophoretic migration. The use of short amplicons has several advantages. First, a broader range of short conserved regions is likely to be found in highly variable targets such as HIV. Second, short amplicons are less likely to have secondary structures which impede amplification.

In additional embodiments, this invention permits the use of two or more distinct probes, either through two enabled primers or an enabled primer and a labeled probe, to provide additional advantages. Primarily, the signal generated by the target nucleic acid sequence can effectively be doubled. Greater specificity can also be achieved by requiring two recognition events, permitting, for example, the subtyping of alleles. With the enabled primer embodiments, true multiplexing is possible. True multiplexing can be achieved using enabled primers that are labeled with different signaling molecules. Prior art probeless methods do not multiplex well because they rely upon methods which distinguish the multiple targets based upon their different lengths. These methods are inherently not quantitative.

In the present invention, a sample or specimen is provided which is suspected of containing the particular "target nucleic acid" sequence of interest. The target nucleic acid contained in the sample may be first reverse transcribed (RT) into cDNA, if isolated as single-stranded RNA or it may be isolated as double-stranded genomic DNA. The cDNA or genomic DNA is then denatured, using any suitable denaturing method, including physical, chemical, or enzymatic means, which are known to those skilled in the art. Physical means for strand separation involves heating the nucleic acid until it is completely denatured. Typical heat denaturation involves the use of temperatures between 80° C. and 100° C., for 3 to 10 minutes. The target nucleic acid may exist in a single-stranded form in the sample, such as, for example, single stranded RNA or DNA viruses and only moderate heating may be necessary to alleviate secondary fold back structures.

The denatured nucleic acid strand(s) are then incubated with preselected oligonucleotide primers and a probe under hybridization or reaction conditions which enable the binding of the primers and probe(s) to the single nucleic acid strands. The primers are selected so that their relative positions along a duplex sequence are such that an extension product produced from one primer serves as a template for the extension of the other primer to yield a replicate chain of defined length, when the extension product is separated from its template (complement) under subsequent denaturation conditions.

Because the complementary nucleic acid strands synthesized are longer than either the probe or primer, the strands have more points of contact and thus a greater chance of finding each other over any given period of time. To prevent reannealing of the longer template, a high molar excess of probe and primer(s) are employed to help sway the hybridization kinetics toward primer and probe annealing rather than template reannealing.

In embodiments not employing an enabled primer, the design of the amplification primers follows generally conventional rules. The primer(s) length must be adequate to prime the synthesis if extension products in the presence of the reaction conditions. The length and composition of the primer is dependent on many factors, including temperature of the reaction, composition of the primer, the position of the probe annealing site to the primer annealing site, and the ratio of primer to probe concentration. Depending on the complexity of the target sequence, the oligonucleotide primers(s) typically contains about 15–30 nucleotides, although it may contain more or fewer nucleotides. The primers must be sufficiently complementary to selectively anneal to their respective strands and form stable duplexes. The primers used are selected to be completely complementary to the different strands of each specific sequence to be amplified. One skilled in the art may select or design primers that have non-complementary sequences on the 5' end, such as restriction enzyme digestion sequences, although the 3' end must maintain its complementarity to insure proper extension and amplification by the DNA polymerase.

In certain embodiments of this invention, the labeled probe must be first annealed to its complementary nucleic acid target before the primers anneal. The activity of the RNase H must supersede the DNA polymerase activity, allowing the cleaved probe fragments to dissociate from the nucleic acid target, as to not interfere with the primer extension and amplification of the nucleic acid target region. Suitable means for adjusting the melting temperature of the probes of this invention are described above.

In certain embodiments, it may be desirable to provide a second probe complementary to a different target sequence. Such a probe should have a label that generates an independently detectable signal. The probes may be designed to have different but compatible melting temperatures based on these techniques.

Template-dependent extension of the oligonucleotide primers(s) is catalyzed by a polymerizing agent in the presence of adequate amounts of the four deoxyribonucleoside triphosphates (dATP, dGTP, dCTP, and dTTP) or analogs discussed above, in a reaction medium which is comprised of the appropriate salts, metal cations and pH buffering system. Suitable polymerizing agents are enzymes known to catalyze primer and template-dependent DNA synthesis and may possess the 5' to 3' nuclease activity. Known DNA polymerases include, for example, E. coli DNA polymerase I, Thermus thermophilus (Tth) DNA polymerase, Bacillus stearothermophilus DNA polymerase, Thermococcus littoralis DNA polymerase, and Thermus aquaticus (Taq) DNA polymerase. The reaction conditions for catalyzing DNA synthesis with these DNA polymerases are well known in the art. To be useful in the present invention, the RNase H must efficiently cleave the ribo- or chimeric oligonucleotide probe and release labeled fragments so that the signal is directly or indirectly generated.

The products of the synthesis are duplex molecules consisting of the template strands and the primer extension strands, which include the target sequence. By-products of this synthesis are labeled oligonucleotide fragments which consist of a mixture of mono-, di-, and larger nucleotide fragments. Repeated cycles of denaturation, labeled probe and primer annealing, and primer extension and cleavage of the labeled probe result in the exponential accumulation of the target region defied by the primers and the exponential generation of labeled fragments. Sufficient cycles are run to achieve a detectable species of label, which is generally several orders of magnitude greater than background signal.

In a preferred method, the PCR reaction is carried out as an automated process which utilizes thermostable enzymes. In this process the reaction mixture is cycled through a denaturing step, a probe and primer annealing step, and a synthesis step, whereby cleavage and displacement occurs simultaneously with primer dependent template extension. A DNA thermal cycler, such as the commercially available machine from Perkin-Elmer/ABI Instruments, which is specifically designed for use with a thermostable enzyme, may be employed.

The oligonucleotide primers and labeled probes may be prepared by a number of methods. Methods for preparing oligonucleotides (deoxy-, ribo-, and chimeric) of a specific sequence are known in the art, and include, for example, cloning and restriction of appropriate sequences, direct automated chemical syntheses and enzymatically. Such techniques include, for example, the phosphotriester method, the phosphodiester method, the diethylphosphoramidate method, and the solid support method.

The composition of the probes can be designed to inhibit nuclease activity. The incorporation of modified phosphodiester linkages (e.g., methyl phosphorylthioate or methylphosphonates) in the labeled probe during chemical synthesis may be used to prevent cleavage at a selected site. Depending on the length of the probe, the composition of its 5' complementary region, and the position of the label, one can design a probe to preferentially favor the generation of short or long labeled probe fragments for use in the practice of the invention. Great flexibility in the modification of the probes of this invention is possible so long as a the probe/target sequence duplex offers an enzymatically cleavable region. Fore example, RNase H requires a 3–6 base pair RNA:DNA sequence.

Temperature stable polymerases are preferred in this automated process because the preferred way of denaturing the double stranded extension products is by exposing them to a high temperature (about 95° C.) during the PCR cycle. For example, U.S. Pat. No. 4,889,818 discloses a representative thermostable enzyme isolated from Thermus aquaticus. Additional representative temperature stable polymerases include, e.g., polymerases extracted from the thermostable bacteria, Thermus flavus, Thermus ruber, Thermus thermophilus, Bacillus stearothermophilus (which has a somewhat lower temperature optimum than the others listed), Thermus lacteus, Thermus rubens, Thermatoga maritima, Thermococcus littoralis, and Methanothermus fervidus.

Detection or verification of the labeled oligonucleotide fragments may be accomplished by a variety of methods and may be dependent on the source of the label or labels employed. One convenient embodiment of the invention is to subject the reaction products, including the cleaved label fragments to size analysis. Methods for determining the size of the labeled nucleic acid fragments are known in the art, and include, for example, gel electrophoresis, sedimentation in gradients, gel exclusion chromatography and homochromatography.

During or after amplification, separation of the labeled fragments from the PCR mixture can be accomplished by, for example, contacting the PCR mixture with a solid phase extractant (SPE). For example, materials having an ability to bind oligonucleotides on the basis of size, charge or interaction with the oligonucleotide bases can be added to the PCR mixture, under conditions where labeled, uncleaved oligonucleotides are bound and labeled fragments are not. Such SPE materials include ion exchange resins or beads, such as the commercially available binding particles Nensorb™ (DuPont Chemical Co.), Nucleogen™ (the Nest Group) and hydroxylapatite. In a specific embodiment, if a dual labeled probe comprising a 3' biotin label separated from a 5' label by a nuclease susceptible cleavage site is employed as the signal means, the PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step wherein the PCR mixture has been contacted with a SPE, the SPE material can be removed by filtration, sedimentation or magnetic attraction leaving the labeled fragments free of uncleaved labeled oligonucleotides and available for detection.

Reagents employed in the methods of the invention can be packaged into diagnostic kits. Diagnostic kits include the labeled oligonucleotides and the primers together or in separate containers. If the oligonucleotide is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

EXAMPLES

Experiment 1

This example demonstrates the ability of the invention to discriminate between sequences having only a single base mismatch. The target sequence is taken from the methylenetetrahydrofolatereductase (MTHFR) gene. Two probes were constructed representing two natural alleles differing at a single base while the target nucleic acid sequence represents one of the two naturally occurring alleles. The two probes are perfectly complementary to one of each of the two alleles. Probes are synthesized of 2'O methyl RNA except for the region in italics which is natural RNA. The varied base between the two sequences occurs at the third base in the native RNA stretch of five bases. Amplification was carried out using conventional PCR techniques:

Forward Primer

GACCTGAAGCACTTGAAGGAGAA/SEQ ID NO. 1

Reverse Primer

AAAGCGGAAGAATGTGTCAGC/SEQ ID NO. 2

Probes
Matched

GUCUCUGCGGGAGCCGAUUUCAUCAUCAC/SEQ ID NO. 3

Labeled at 5' with FAM and at 3' with TAMRA
The italicized region is natural RNA and all other regions are 2'O-methyl RNA
Mismatched

GUCUCUGCGGGAGUCGAUUUCAUCAUCAC/SEQ ID NO. 4

Labeled at 5' with FAM and at 3' with TAMRA
The italicized region is natural RNA and all other regions are 2'O-methyl RNA
Target Sequence CTTTGAGGCTGACCTGAAGCACTTGAAG-
GAGAAGGTGTCTGCGGGAGC-
CGATTTCATCATCACG-
CAGCTTTTCTTTGAGGCTGACACATTCTTCCGCT
TTGTGAAGGCATGCACCGACAT/SEQ ID NO. 5

Figure 1:
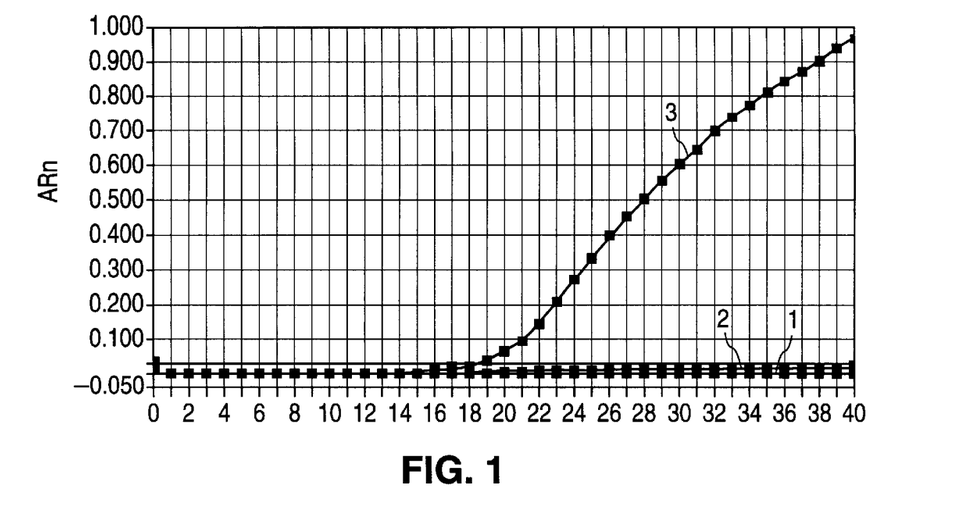
FIG. 1 is a graphical representation of amplification reactions embodying features of the invention that show discrimination between sequences having a single base mismatch.

Conditions
4 Cycles
  95° C. 15 seconds
  58° C. 30 seconds
40 Cycles
  90° C. 10 seconds
  58° C. 30 seconds As shown in FIG. 1, three separate amplification plots were obtained. Curve 1 corresponds to a no-target control run with the matched probe. Curve 2 shows the results with target nucleic acid sequence with the probe mismatched at a single base while curve 3 shows the results with the matched probe. While good signal generation was obtained with the matched probe, the mismatched probe shows virtually no signal generation.

Experiment 2

This example shows an enabled primer embodiment of the invention. The target sequence is taken from the MTHFR gene. The enabled primer is synthesized of DNA except for the region in italics which is natural RNA. The enabled primer was subjected to PCR amplification both in the presence and absence of the target sequence. No "hot start" conditions were employed and the annealing temperature was lowered to 48 degrees to enhance any tendency for primer-dimer formation.

Enabled Primer

AGGAGAAGGTCTCTGCGGGAGCCGGAU/SEQ ID NO. 6

The 5' end is labeled with FAM and the 3' end with TAMRA
The italicized region is natural RNA and all other regions are DNA.

Reverse Primer

AAAGCGGAAGAATGTGTCAGC/SEQ ID NO. 2

Template

CTTTGAGGCTGACCTGAAGCACTTGAAG-
GAGAAGGTGTCTGCGGGAGC-
CGATTTCATCATCACG-
CAGCTTTTCTTTGAGGCTGACACATTCTTCCGC
TTTGTGAAGGCATGCACCGACAT/SEQ ID NO. 5

Figure 2:
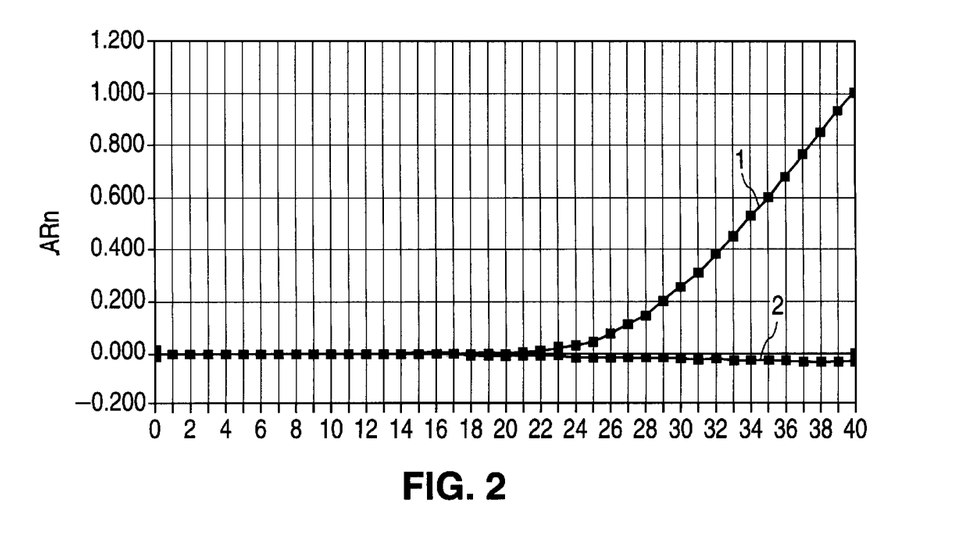
FIG. 2 is a graphical representation of amplification reactions performed with an enabled primer of the invention.

Conditions
4 Cycles
  95° C. 15 seconds
  48° C. 30 seconds
  58° C. 30 seconds
  68° C. 30 seconds
40 Cycles
  90° C. 10 seconds
  48° C. 30 seconds
  58° C. 30 seconds
  68° C. 30 seconds The signal generation of the two amplifications is shown in FIG. 2. Curve 1 shows good amplification and signal when the enabled primer was included with the target sequence. Curve 2 shows that in the absence of target sequence there was virtually no signal generated. Thus, using the enabled primer of the invention, there was no demonstrable primer-dimer formation despite the absence of "hot start" conditions and the lowered reaction temperature of 48° C.

Experiment 3

This example contrasts the use of an enabled primer with a conventional primer. The forward and reverse primers were perfectly complementary to opposite strands of a target nucleic acid sequence from a region of the MFR gene. One of the forward primers is an enabled primer while the other is a conventional PCR primer. The PCR conditions selected were likely to produce primer-dimers: no "hot start" conditions employed and a lowered annealing temperature of 48° C.

Enabled Primer

AGGAGAAGGTCTCTGCGGGAGCCGGAU/SEQ ID NO.6

The 5' end is labeled with FAM and the 3' end with TAMRA

The italicized region is natural RNA and all other regions are DNA.

Conventional Primer

AGGAGAAGGTCTCTGCGGG/SEQ D NO.7

Reverse Primer

AAAGCGGAAGAATGTGTCAGC/SEQ ID NO.2

Target Sequence

CTTTGAGGCTGACCTGAAGCACTTGAAG-
       GAGAAGGTGTCTGCGGGAGC-
       CGATTTCATCATCACGCAGCTTTTCTTT-
       GAGGCTGACACATTCTTCCGCTTTGTGAAGGCA
       TGCACCGACAT/SEQ ID NO.5

Figure 3:
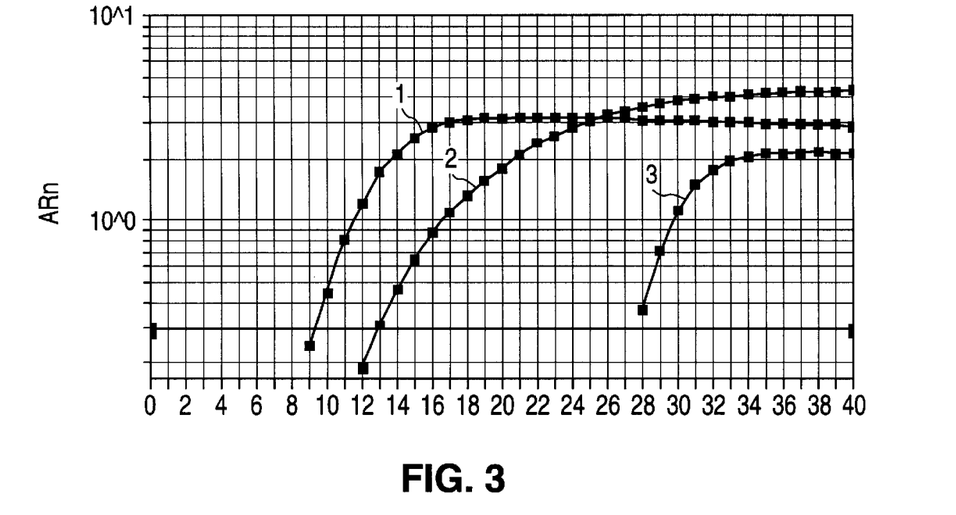
FIG. 3 is a graphical representation comparing amplification reactions performed with the enabled primers of the invention and conventional primers.

FIG. 3 shows the results of 4 amplification runs, the enabled primer and the conventional primer with and without the target sequence. Signal was detected with Syber Green. Curves 1 and 2 show the conventional and enabled primers run with the same concentration of MTHFR template, respectively. Curve 3 represents the standard primer with no template demonstrating the formation of primer-dimers. Conversely, no amplification was detected when the enabled primer was amplified without target sequence. This demonstrates that hot start conditions are not required with the enabled primer.

Example 4

In this example, a serial dilution of an extraction of tissue-culture grown CMV was amplified. Conventional PCR amplification conditions were employed.

Target Sequence

Extracted viral DNA

Forward Primer

TCCTCTGATTCTCTGGTGTCACC/SEQ D NO.8

Reverse Primer

GATCACTGTTCTCAGCCACAATTACT/SEQ ID NO.9

Probe

CCCUGUACCCGCGACUAUCCCUCUGUCAISEQ ID NO.10

Figure 4:
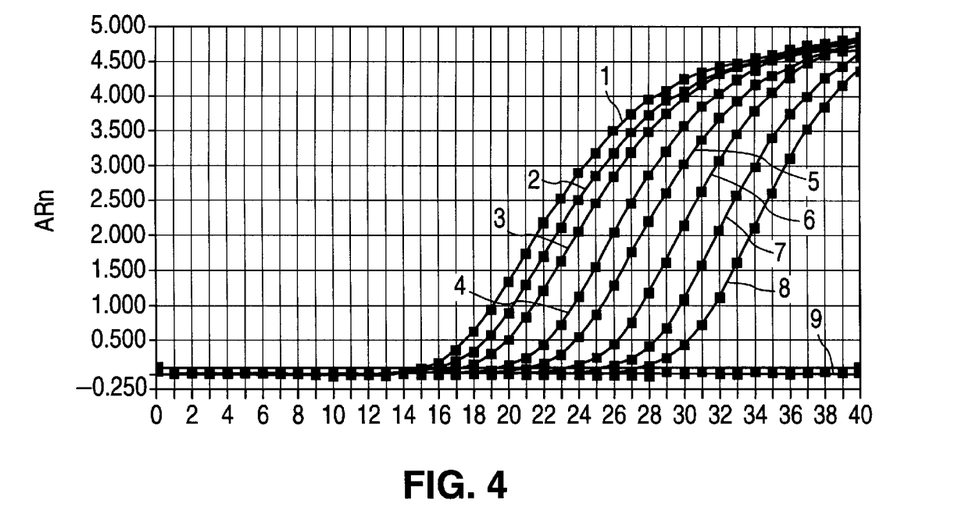
FIG. 4 is a graphical representation of amplification reaction of the invention demonstrating that non-specific probe cleavage does not occur and that the invention functions over a wide range of target nucleic acid concentrations.

All natural RNA bases labeled at the 5' end with FAM and at the 3' end with TAMRA Conditions     95° C. 9 minutes
4 Cycles
    95° C. 15 seconds
    55° C. 1 minute and 10 seconds
    72° C. 20 seconds
40 Cycles
    90° C. 10 seconds
    70° C. 10 seconds
    55° C. 1 minute and 10 seconds
    72° C. 20 seconds The amplification products were subjected to conventional guanidinium thiocyanate extraction using phenol-chloroform. FIG. 4 shows the signal generated by the amplification, with each curve 1–8 representing a four-fold serial dilution of the CMV extract. Curve 9 shows that no signal was generated when the probe was used in a no-target sequence control amplification. This example demonstrates that non-specific RNase H-mediated cleavage does not occur and interfere with quantitative signal generation.

The invention has been described with a particular view to the presently preferred embodiments. However, it will be obvious that certain changes and modifications may be practiced within the scope of the invention by those of skill in the art.

---

We claim:

1. A process for amplifying a target nucleic acid sequence comprising the steps of:
   a) providing a nucleotide amplification reaction mixture containing the target nucleic acid sequence configured to amplify the target nucleic acid sequence;
   b) within the nucleotide amplification reaction mixture, contacting the target nucleic acid sequence with a first probe that is complementary to the target nucleic acid sequence and comprises at least one releasable probe portion, wherein the first probe and the target nucleic acid sequence form a duplex having an enzymatically cleavable region wherein enzymatic cleavage of the first probe results in the release of a releasable probe portion; and
   c) contacting the first probe and target nucleic acid sequence duplex with an enzyme capable of cleaving the enzymatically cleavable region to release a releasable probe portion and d) making sequential measurements of the release of the releasable probe portion to kinetically characterize the target DNA sequence wherein steps b)–d) are performed in a single reaction mixture.

2. The process of claim 1 wherein a first label is attached to a probe portion of the first probe, further comprising the step of detecting the label after release of a releasable probe portion.

3. The process of claim 2, wherein a second label is attached to the first probe, the first and second labels comprise interactive signal-generating moieties such that attachment of the labels causes the second label to suppress detection of the first label and release of the releasable probe portion allows detection of the first label.

4. The process of claim 1 further comprising detecting the first probe and target nucleic acid sequence duplex.

5. The process of claim 4 wherein detecting the duplex comprises adding a double-stranded DNA binding agent.

6. The process of claim 1, wherein the first probe comprises a DNA:RNA:DNA chimera and wherein the enzyme comprises RNase H.

7. The process of claim 1, wherein the first probe comprises a DNA:RNA chimera and wherein the enzyme comprises RNase H.

8. The process of claim 1, wherein the first probe comprises at least one sequence of modified RNA bases that are not cleavable by RNase H and at least one RNA base that is cleavable by RNase H and wherein the enzyme comprises RNase H.

9. The process of claim 1, wherein the amplification reaction mixture is a polymerase chain reaction mixture.

10. The process of claim 1, wherein the first probe is configured to have an enzymatically cleavable region only if the first probe and target nucleotide sequence is perfectly matched.

11. The process of claim 10, wherein providing a nucleotide amplification reaction mixture further comprises providing a nucleotide amplification reaction mixture containing at least one additional nucleic acid sequence wherein the additional nucleic acid sequence is not perfectly matched to the target nucleic acid sequence and further comprising the step of blocking amplification of the additional nucleic acid sequence by contacting the additional nucleic acid sequence with the first probe wherein the first probe and the additional nucleic acid sequence form a duplex that does not have an enzymatically cleavable region.

12. The process of claim 1, wherein the step of contacting the target nucleic acid sequence with a first probe further comprises contacting the target nucleic acid sequence with the first probe wherein the first probe further comprises a nonreleasable probe fragment that is configured to be a primer in the amplification reaction mixture and the releasable probe fragment is configured to block a nucleotide amplification reaction.

13. The process of claim 12, wherein the step of providing a nucleotide amplification reaction mixture further comprises providing the nucleotide amplification reaction mixture wherein the nucleotide amplification reaction mixture further comprises at least one additional nucleic acid sequence and wherein the additional nucleic acid sequence is not perfectly matched to the target nucleic acid and further comprising the step of blocking amplification of the additional nucleic acid sequence by contacting the first probe and the additional nucleic acid sequence wherein the first probe and the additional nucleic acid sequence form a duplex that does not have an enzymatically cleavable region.

14. The method of claim 1, further comprising the step of adding a second probe to the nucleotide amplification reaction mixture, wherein the second probe is complementary to a different region of the target nucleic acid sequence than the first probe and comprises a releasable probe portion, wherein the second probe and the target nucleic acid sequence form a duplex having an enzymatically cleavable region wherein enzymatic cleavage of the second probe results in the release of the releasable probe portion.

15. The method of claim 14, wherein a label is attached to a probe portion of the second probe.

16. A method for the detection of a target nucleic acid sequence in a sample comprising the steps of:

a) amplifying the target DNA sequence with a polymerase chain reaction amplification reaction;

b) concurrently with step a), contacting and annealing a probe comprising a ribo-oligonucleotide attached to a first label with a sample containing a target nucleic acid sequence having a region complementary to the probe;

c) cleaving at least one of the ribonucleotides of the annealed probe with a ribo-nucleic acid nuclease capable of hydrolyzing ribonucleotides in a double stranded RNA:DNA duplex to release labeled ribo-oligonucleotide fragments; and d) generating a signal from the released labeled ribo-oligonucleotide fragments that characterizes the target nucleic acid sequence; wherein steps a)–d) are performed in a single reaction mixture.

* * * * *